United States Patent [19]

Jerde et al.

[11] Patent Number: 4,491,499

[45] Date of Patent: Jan. 1, 1985

[54] OPTICAL EMISSION END POINT DETECTOR

[75] Inventors: Leslie G. Jerde, Hopewell Township, Mercer County; Earl R. Lory, Pennington; Kevin A. Muething, Hillsborough Township, Somerset County; Len Y. Tsou, Lawrence Township, Mercer County, all of N.J.

[73] Assignee: AT&T Technologies, Inc., New York, N.Y.

[21] Appl. No.: 594,629

[22] Filed: Mar. 29, 1984

[51] Int. Cl.³ .......................... C23F 1/00; B44C 1/22; C03C 15/00; C03C 25/06

[52] U.S. Cl. ........................ 156/626; 156/627; 156/643; 156/646; 204/192 E; 204/298; 356/437; 356/222

[58] Field of Search ............... 156/626, 627, 643, 646, 156/656, 659.1, 665, 345; 204/164, 192 E, 298; 356/345, 381, 437, 218, 222, 229

[56] References Cited

U.S. PATENT DOCUMENTS

| | | | |
|---|---|---|---|
| 4,198,261 | 4/1980 | Busta et al. | 156/626 |
| 4,201,579 | 5/1980 | Robinson et al. | 430/323 |
| 4,208,240 | 6/1980 | Latos | 156/627 |
| 4,263,088 | 4/1981 | Gorin | 156/626 |
| 4,263,089 | 4/1981 | Keller | 156/627 |
| 4,317,698 | 3/1982 | Christol et al. | 156/626 |
| 4,345,968 | 8/1982 | Coe | 156/627 |
| 4,352,725 | 10/1982 | Tsukada | 204/192 E |
| 4,377,436 | 3/1983 | Donnelly et al. | 156/626 |
| 4,380,488 | 4/1983 | Reichelderfer et al. | 156/643 |

*Primary Examiner*—William A. Powell
*Attorney, Agent, or Firm*—D. J. Kirk

[57] ABSTRACT

A method for determining the optimum time at which a plasma etching operation should be terminated. The optical emission intensity ($S_1$) of the plasma in a narrow band centered about a predetermined spectral line, indicative of the gas phase concentration of a plasma etch product or reactant species. The optical emission intensity ($S_2$) of the plasma in a wide band centered about the predetermined spectral line, indicative of a background emission signal is also monitored. The intensity ($S_{1L}$) of the spectral line is then determined in accordance with the equation $S_{1L} = S_1 - k(\alpha S_2 - S_1)$. The etching process is terminated when the monitored signal intensity ($S_{1L}$) or its time derivative reaches a predetermined value.

12 Claims, 1 Drawing Figure

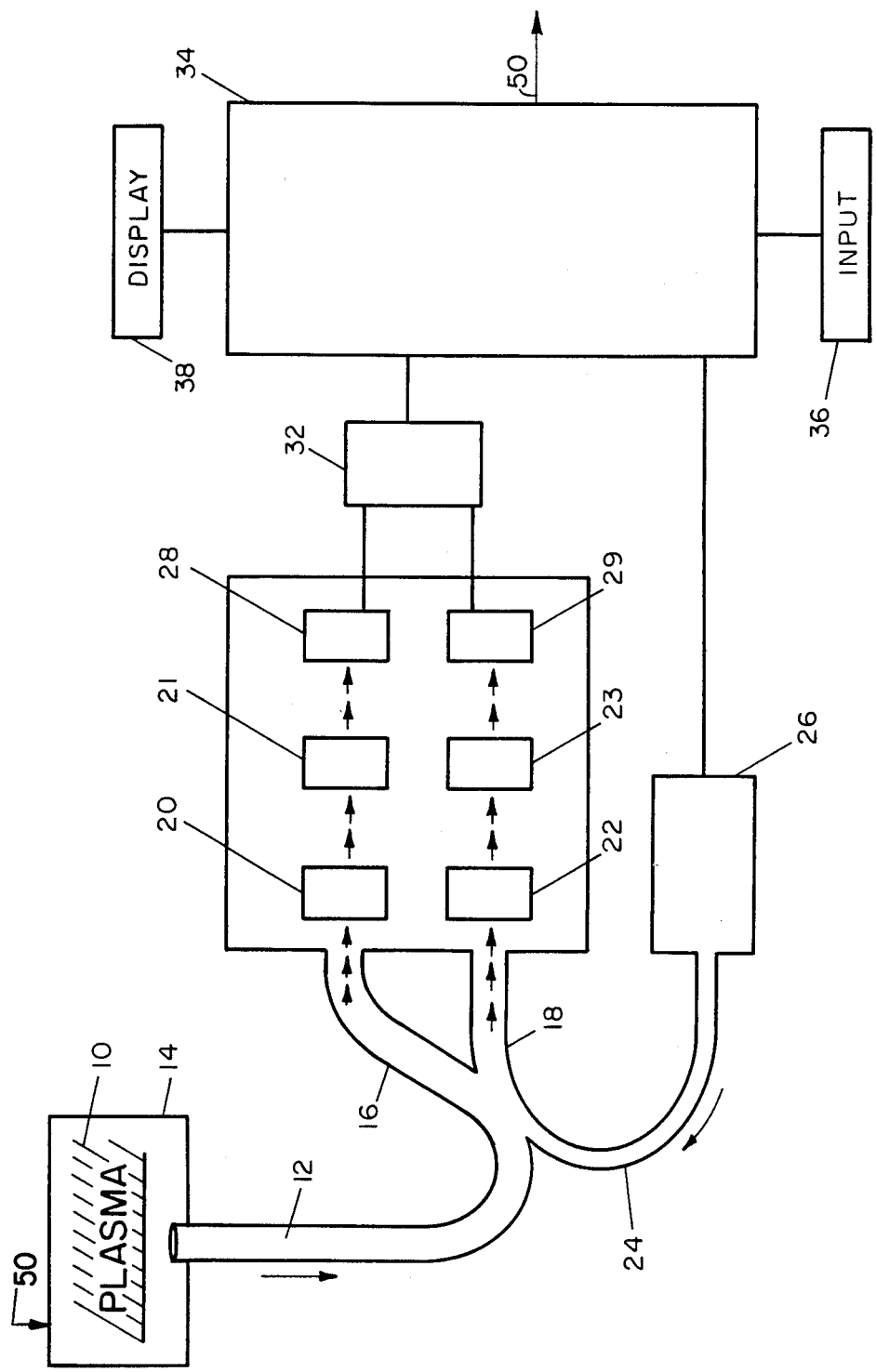

OPTICAL EMISSION END POINT DETECTOR

TECHNICAL FIELD

The instant invention is directed to a method and apparatus for determining the time at which a plasma etching operation should be terminated.

BACKGROUND OF THE INVENTION

The etching of silicon wafers by "plasma" or "dry" techniques is still more of an art than a science. A well defined etching process trys to meet four main criteria simultaneously: (1) high etch rate(s) of the material or materials to be patterned, (2) low etch rates of the mask and etch stop materials, (3) good anisotropy and (4) good etch rate uniformity. Often it is not possible to achieve all four at the same time. In situations for which the selectivity and anisotropy are merely adequate, it is desirable to etch only until the pattern is defined. Overetching leads to unacceptable line width control. Consequently one wants to stop the etching as close to the point of completion as possible.

One of the most useful methods for monitoring the etching of a wafer is to monitor the amplitude intensity of optical emission from the plasma discharge. Many processes have particular spectral lines or regions which are driven by the presence of some chemical constituent in the plasma such as a reactant species or a species produced as an etching by-product. By tracking the intensity at the wavelength of these species in the plasma, one has some idea about the concentration of these species in the plasma which is directly related to the status of the etching process.

One known apparatus monitors a single spectral line at a time. However, it monitors that line with two channels. The first channel monitors the light intensity in a narrow region about the predetermined spectral line while the second channel monitors the light intensity in a substantially larger bandwidth which is close to, but does not include, the spectral line. Accordingly, the first channel monitors the intensity of the line of interest while the second channel monitors the background signal. By subtracting the background signal from the first channel signal the intensity of the desired line may be obtained.

If the emisson from an etching plasma has a line in the region of the spectrum with low background or, more accurately, if the line strength is very high with respect to the background, then it is a simple matter to monitor the process. However, when the spectral emission does not have a line strength that is substantially higher than the background, problems arise in distinguishing the line from the background resulting in underetching or overetching of the devices being processed.

SUMMARY OF THE INVENTION

The instant method for determining the time at which a plasma etching operation should be terminated overcomes the foregoing problem. The method comprises the steps of: monitoring the optical emission intensity ($S_1$) of the plasma, in a narrow band centered about a predetermined spectral line, indicative of the gas phase concentration of a plasma etch reactant or product; monitoring the optical emission intensity ($S_2$) of the plasma, in a wide band centered about the predetermined spectral line, indicative of an optical background emission signal; determining the intensity ($S_{1L}$) of the spectral line in accordance with the formula: $S_{1L} = S_1 - k(\alpha S_2 - S_1)$, where k=a constant set to a value to give optimum results; and $\alpha$=a constant determined by optical and electrical responses of the two signal amplification channels. The etching process is terminated when ($S_{1L}$) and/or its time derivative achieves a predetermined value.

BRIEF DESCRIPTION OF THE DRAWINGS

The sole figure is a schematic diagram of apparatus used to implement the instant invention.

DETAILED DESCRIPTION

The figure depicts one type of apparatus for monitoring the intensity of a spectral line emanating from a plasma 10 associated with the gas phase concentration of a plasma etch product or reactant species associated with the plasma etching process. The light associated with the plasma 10 is picked up and guided by a fiber optic bundle 12 which projects into a plasma etching chamber 14 wherein articles (not shown) are being etched. The fiber bundle 12 splits equally into first and second channels 16 and 18, respectively. The light in first channel 16 passes through an optical unit 20 and an interference filter 21 while the second channel 18 passes through an optical unit 22 and an interference filter 23. Additionally there is a second input bundle 24 of lightguide fibers which is comprised of a plurality of fibers which is also split 50/50 in a randomized fashion into the first and second channels 16 and 18. The second input bundle 24 is used to inject light of a known intensity from a test source 26 into the system for calibration purposes.

The light passing along channel 16 through the optical unit 20 and the filter 21 is then directed onto an ultraviolet enhanced photovoltaic detector 28 which converts the light into a voltage while the light passing along channel 18 through the optical unit 22 and the filter 23 impinges on a detector 29. After some analog smoothing, these voltages pass to a data acquisition module 32 which does real time processing to produce a voltage indicative of the strength of the spectral line of interest. This voltage is digitized in the module 32 and forwarded to a microprocessor 34.

Parameters associated with the end point (e.g., maximum time to etch before terminating automatically and percent of over etch) are entered into the microprocessor 34 via the input device 36 which may be, for instance, sets of thumbwheel switches or the like. Display of messages and data occurs on a 16 character alphanumeric LED dot matrix display 38.

The primary function of the microprocessor 34 is to monitor the time evolution of the optical emission of the intensity of a select wavelength and to repeatably determine when the etching has reached completion. A stop signal is then generated by the microprocessor 34 and forwarded to the chamber 14 over the line 50.

OPTICAL PROCESSING

A. No Background Subtraction

If one must monitor emission from an etching plasma 10 that has a spectral line in a region of the spectrum with low background or, more accurately, if the line strength is very high with respect to the background, then it is a simple matter to monitor the process. Physically all that is required is an interference filter to select the line to be monitored, a photodetector and an amplifier. If we neglect the behavior of the amplifier, then the signal intensity output of such a unit can be represented by $$S = \int_0^\infty I(\lambda,t)R(\lambda,t)T(\lambda)d\lambda \quad (1)$$

where I ($\lambda$,t) is the total emission intensity, T($\lambda$) represents the transmission characteristics of the line filter and R ($\lambda$,t) is the response function of the photodetector. Usually the transmission function of the interference filter can be represented as a Gaussian distribution. In practice the width can be made as small as 10A Full Width, Half Maximum (FWHM) and the center can be located with an accuracy of ±1A. The detector function R($\lambda$,t), of course, depends on the photodetector used. In a preferred embodiment a silicon photovoltaic detector, model HUV-4000B manufactured by EG&G Company, Princeton, N.J., was used. In addition this device has a built-in amplifier so that the complete unit compares favorably with a photomultiplier tube.

For this case, where the line strength is very high with respect to the background, the use of two channels 16 and 18, shown in FIG. 1, is not required. The equipment described here is still useful, but one can disable or block one of the channels.

B. With Background Subtraction

When it becomes necessary to monitor a spectral emission line which does not have a strength large compared to the background, one must try to correct for the background. Mathematically, the total spectral intensity I($\lambda$,t) can be set forth as the addition of two terms, the background intensity $I_B(\lambda,t)$ and the line intensity $I_L(\lambda,t)$. If we look at the intensity ($S_1$) from a single interference filter/detector package (e.g., channel 16), the result is $$S_1 = \int_0^\infty \{I_B(\lambda,t) + I_L(\lambda,t)\} T(\lambda)R(\lambda,t)d\lambda. \quad (2)$$

or $$S_1 = S_{1B} + S_{1L} = \int_0^\infty I_B(\lambda,t)T(\lambda)R(\lambda,t)d\lambda + \int_0^\infty I_L(\lambda,t)T(\lambda)R(\lambda,t)d\lambda \quad (3)$$

The intensity has a component from the background ($S_{1B}$) and a component from the line ($S_{1L}$) with $S_{1L} < S_{1B}$.

One approach to distinguish the line strength intensity from the background is to use the second channel 18 in addition to the first channel 16. The second channel 16 should be very similar to the first except that the interference filter 23 has a much wider spectral bandpass and does not contain the spectral line of interest. Then if we consider the intensity on the second channel 16, we have $S_2 = S_{2B} + S_{2L}$, i.e., an intensity due to the background and an intensity due to the line. The contribution to $S_2$ from the background is much greater than any contribution of the line, consequently, $S_2$ is just representative of the background. Then it is possible to extract the intensity due to the line from $S_1$. For example, $$S_{1L} = S_1 - k \cdot S_2 \quad (4)$$

where k is a parameter which scales the background seen by channel 2 to that seen by the first channel 16. Physically k can be found by observing an etching plasma 10. When the line that one is watching decreases in intensity at the end point, then $S_{1L}$ may be set to zero in equation (4) to yield:

$$k = \frac{S_1}{S_2} \text{ at } t = t_{end\ point} \quad (5)$$

It should be noted that the background signal varies from run to run and even during a run, the parameter k cannot be determined a priori. In fact, the best procedure is probably to use the k from the last run to monitor the line strength on the next run. In this way, the end point detector can adjust itself as the conditions in the reactor vary with time.

C. Enhanced Background Subtraction

The instant technique provides a method of determining the etching end point which is more accurate than the foregoing procedures. In this technique, the two interference filters 28 and 29 are centered on the same line and the bandwidth of the filter 29 is two to three times wider than the filter 28. Each channel 16 and 18 has a non-trivial component due to the line,
Channel 16:

$$S_1 = S_{1B} + S_{1L} \quad (6)$$

Channel 18:

$$S_2 = S_{2B} + S_{2L} \quad (7)$$

Multiplying $S_2$ by a factor $\alpha$ and subtracting yields $$\alpha S_2 - S_1 = \{\alpha S_{2B} - S_{1B}\} + \{\alpha S_{2L} - S_{1L}\} \quad (8)$$

There is a factor $\alpha$ such that the term $$\alpha \cdot S_{2L} - S_{1L} = 0 \quad (9)$$

Physically the factor $\alpha$ is the product of two terms: (1) the gain ratio of the amplifiers of the two channels, and (2) the ratio of the transmissions of the two interference filters at the line wavelength. Both of these are easily found. Thus the difference of the two intensities with the appropriate scaling is a quantity which depends only on the background in the spectral region around the line of interest. That is, $$\alpha S_2 - S_1 = \alpha S_{2B} - S_{1B} \text{ tm (10)}$$

which is proportional to the background only. Now the line strength can be extracted from $S_1$ by using equation (4) with $S_2$ replaced by the more accurate background strength represented by equation (10):

$$S_{1L} = S_1 - k(\alpha S_2 - S_1) \quad (11)$$

The term $\alpha S_2 - S_1$ is a sensitive measure of the background and, because of the similarity of the two interference filters, this samples the background only in the immediate vicinity of the line being monitored.

When ($S_{1L}$) and/or its time derivative achieves a predetermined value the etching process is terminated. The parameter k will vary from run to run and even during a run. Therefore k can be found for the case of a decreasing line strength (i.e., when $S_{1L}=0$) by taking $$k = \frac{S_1}{\alpha S_2 - S_1} \quad (12)$$

The parameter $\alpha$ is a very slowly varying function of time and will vary predominantly due to gain drifts in the electronics. This can be accounted for by having instrumentation capable of measuring its own gain. Once again $\alpha$ is just the product of two factors, the ratio of the gains of the two channels and the ratio of the transmissions of the interference filters.

The optics 20 and 22 consist of Fresnel lens made of acrylic with a 25.4 mm focal length and 30 mm diameter. This lens collimates the light output from the fiber in channels 16 and 18. The light then passes through the narrow band pass interference filters 21 and 23. The specifications of the filters 21 and 23 depend on the spectral line being monitored. In an exemplary embodiment (monitoring aluminum) the filters 21 and 23 are centered at 396.1 nm with bandpasses of 1 nm FWHM for filter 21 and 3 nm FWHM for filter 23. A neutral density filter may be used to adjust the transmission of the wideband filter 23 so that it was comparable to the narrow one. After passing through the interference filters 21 and 23, the light signal is converted to a voltage proportional to the intensity of the light by the detectors 28 and 29.

It is to be understood that the embodiments described herein are merely illustrative of the principles of the invention. Various modifications may be made thereto by persons skilled in the art which will embody the principles of the invention and fall within the spirit and scope thereof.

What is claimed is:

1. A method for determining the time at which a plasma etching operation should be terminated, comprising the steps of:
    monitoring the optical emission intensity ($S_1$) of the plasma, in a narrow band centered about a predetermined spectral line, indicative of the gas phase concentration of a plasma etch product or reactant species;
    monitoring the optical emission intensity ($S_2$) of the plasma, in a wide band centered about the predetermined spectral line, indicative of an optical background emission signal;
    determining the intensity ($S_{1L}$) of the spectral line in accordance with the equation:

$$S_{1L} = S_1 - k(\alpha S_2 - S_1)$$

where:
    k = a constant set to a value to give optimum results; and
    $\alpha$ = a constant determined by optical and electrical responses of the two signal amplification channels; and
    terminating the etching process when ($S_{1L}$) achieves a predetermined value.

2. The method as set forth in claim 1, wherein: the material being etched is aluminum.

3. The method as set forth in claim 1, wherein: the wide band is approximately three times wider than the narrow band.

4. The method as set forth in claim 1, wherein: the plasma etching process is terminated when the time derivative of ($S_{1L}$) achieves a predetermined value.

5. The method as set forth in claim 2, wherein: the narrow band is 1 nm and the wide band is 3 nm; and
    both bands are centered at 396.1 nm.

6. The method as set forth in claim 1, comprising the step of:
    determining the value of the constant k when $S_{1L}=0$ using the following formula:

$$k = \frac{S_1}{\alpha S_2 - S_1}.$$

7. An apparatus for determining the time at which a plasma etching operation should be terminated, comprising:
    means for monitoring the optical emission intensity ($S_1$) of the plasma, in a narrow band centered about a predetermined spectral line, indicative of the gas phase concentration of a plasma etch product or reactant species;
    means for monitoring the optical emission intensity ($S_2$) of the plasma, in a wide band centered about the predetermined spectral line, indicative of an optical background emission signal;
    means for determining the intensity ($S_{1L}$) of the spectral line in accordance with the equation:

$$S_{1L} = S_1 - k(\alpha S_2 - S_1)$$

where:
    k = a constant set to a value to give optimum results; and
    $\alpha$ = a constant determined by optical and electrical responses of the two signal amplification channels; and
    means for terminating the etching process when ($S_{1L}$) achieves a predetermined value.

8. The apparatus as set forth in claim 7, wherein: the material being etched is aluminum.

9. The apparatus as set forth in claim 7, wherein: the wide band is approximately three times wider than the narrow band.

10. The apparatus as set forth in claim 7, wherein: the plasma etching process is terminated when the time derivative of ($S_{1L}$) achieves a predetermined value.

11. The apparatus as set forth in claim 8, wherein: the narrow band is 1 nm and the wide band is 3 nm; and
    both bands are centered at 396.1 nm.

12. The apparatus as set forth in claim 7, comprising: means for determining the value of the constant k when $S_{1L}=0$ using the following formula:

$$k = \frac{S_1}{\alpha S_2 - S_1}.$$

* * * * *

UNITED STATES PATENT AND TRADEMARK OFFICE
CERTIFICATE OF CORRECTION

PATENT NO. : 4,491,499
DATED : January 1, 1985
INVENTOR(S) : L. G. Jerde-E. R. Lory-K. A. Muething-L. Y. Tsou It is certified that error appears in the above—identified patent and that said Letters Patent is hereby corrected as shown below:

In the specification, Column 4, line 39, Equation (8),

"$\alpha S_2 - S_1 = \{\alpha S_{2B} - S_{1B}\} + \{\alpha S2L - S_{1L}\}$"

should read $-- \alpha S_2 - S_1 = \{\alpha S_{2B} - S_{1B}\} + \{\alpha S_{2L} - S_{1L}\} --;$ line 53, Equation (10), "$\alpha S_2 - S_1 = \alpha S_{2B} - S_{1B} tm(10)$"

should read $-- \alpha S_2 - S_1 = \alpha S_{2B} - S_{1B} \qquad (10) --.$

Signed and Sealed this

Fourteenth Day of May 1985

[SEAL]

Attest:

DONALD J. QUIGG

Attesting Officer    Acting Commissioner of Patents and Trademarks